United States Patent [19]
Nielsen et al.

[11] Patent Number: 5,846,558
[45] Date of Patent: Dec. 8, 1998

[54] IONICALLY CONDUCTIVE ADHESIVES PREPARED FROM ZWITTERIONIC MATERIALS AND MEDICAL DEVICES USING SUCH ADHESIVES

[75] Inventors: Kent E. Nielsen, Dorchester; Kai Li, Ancaster, both of Canada; Steven S. Kantner, St. Paul, Minn.; Nancy L. Koski, Hudson, Wis.; Albert I. Everaerts, Oakdale, Minn.

[73] Assignee: Minnesota Mining and Manufacturing Company, St. Paul, Minn.

[21] Appl. No.: 618,219

[22] Filed: Mar. 19, 1996

[51] Int. Cl.[6] ............................. A61F 13/02; A61K 9/70
[52] U.S. Cl. ...................... 424/448; 424/443; 424/449
[58] Field of Search .................... 424/405, 407, 424/409, 449, 443, 448, 445; 524/140, 141, 145, 386, 439, 460

[56] References Cited

U.S. PATENT DOCUMENTS

| | | | |
|---|---|---|---|
| 3,770,708 | 11/1973 | Knoepfel et al. | 260/80.73 |
| 3,868,340 | 2/1975 | Keegan et al. | 260/17.4 |
| 4,136,078 | 1/1979 | Doggett et al. | 260/33.2 |
| 4,524,087 | 6/1985 | Engel | 427/2 |
| 4,539,996 | 9/1985 | Engel | 128/640 |
| 4,554,924 | 11/1985 | Engel | 128/640 |
| 4,715,382 | 12/1987 | Strand | 128/640 |
| 4,771,783 | 9/1988 | Roberts | 128/640 |
| 4,846,185 | 7/1989 | Carim | 128/641 |
| 4,848,353 | 7/1989 | Engel | 128/640 |
| 5,012,810 | 5/1991 | Strand et al. | 128/640 |
| 5,133,356 | 7/1992 | Bryan et al. | 128/640 |
| 5,216,048 | 6/1993 | Agarwal et al. | 524/60 |
| 5,276,079 | 1/1994 | Duan et al. | 524/386 |

FOREIGN PATENT DOCUMENTS

| | | | |
|---|---|---|---|
| 0 012 402 | 6/1980 | European Pat. Off. | C09J 3/14 |
| 0 051 935 A2 | 5/1982 | European Pat. Off. | A61F 13/02 |
| 89/07951 | 9/1989 | WIPO | A61L 15/13 |
| 91/15250 | 10/1991 | WIPO | A61L 15/06 |
| 94/26950 | 11/1994 | WIPO | C23C 14/20 |
| 95/20350 | 8/1995 | WIPO | A61B 5/0408 |

OTHER PUBLICATIONS

J.C. Salamone and W.C. Rice, "Polyampholytes", *Encyclopedia of Polymer Science and Engineering,* vol. 11, pp. 514–530).

Liaw et al., *J. Chin.Inst. Chem. Eng.,* 21, 1, (1990).

*Surface Active Agents and Detergents,* vol. II, Chapter 20, Anthony M. Schwartz, James W. Perry, and Julian Berch, Robert E. Krieger Publishing Co., Huntington, New York, 1977.

*Primary Examiner*—Thurman K. Page
*Assistant Examiner*—Kathryne E. Shelborne
*Attorney, Agent, or Firm*—Gary L. Griswold; John H. Hornickel

[57] ABSTRACT

Ionically conductive adhesives are disclosed. The adhesives are prepared from zwitterionic polymers, preferably prepared from zwitterionic monomers. Medical devices, such as biomedical electrodes, skin coverings, and transdermal delivery devices using such adhesives so prepared are also disclosed.

28 Claims, 2 Drawing Sheets

IONICALLY CONDUCTIVE ADHESIVES PREPARED FROM ZWITTERIONIC MATERIALS AND MEDICAL DEVICES USING SUCH ADHESIVES

FIELD OF THE INVENTION

This invention relates to ionically conductive adhesives prepared from zwitterionic materials and medical devices, such as biomedical electrodes, skin coverings, and transdermal delivery devices using such adhesives so prepared.

BACKGROUND OF THE INVENTION

Biomedical electrodes are used for diagnostic and therapeutic purposes including electrocardiographic monitoring and diagnosis, electrosurgery, iontophoretic (electrically enhanced) transdermal delivery of drugs, and defibrillation. In their most basic form these electrodes comprise a conductive medium contacting mammalian skin and a means for electrical communication interacting between the conductive medium and electrical diagnostic, therapeutic, or electrosurgical equipment.

The conductive medium used in these electrodes is generally an ionically conductive adhesive or gel. This adhesive or gel consists of a polar polymeric network which is plasticized with a humectant material such as glycerin or poly(ethylene glycol). Water, a salt, or a drug may also be included depending on the application. Generally a relatively thick layer of adhesive or gel is used (10 to 100 mil (0.25 to 2.5 mm) or greater).

Several different types of hydrophilic polymers are used to prepare conductive adhesives and gels as disclosed in the art. These polymers can be categorized according to the source of the polymer (natural or synthetic) and the charge on the polymer (neutral, positive, or negative).

There is only one known disclosure of a hydrogel prepared with both positive and negative charges on the polymer. PCT Publication WO91/15250 discloses a blend of two different polymers, one anionic and one cationic.

Polymers possessing both positively and negatively charged moieties on the same backbone are known (cf "Polyampholytes", J. C. Salamone and W. C. Rice in *Encyclopedia of Polymer Science and Engineering,* Vol. 11, pp. 514–530)

Further, the use of low levels (20 to 1 weight percent) of zwitterionic monomers in hydrophobic PSA formulations has been disclosed in U.S. Pat. No. 3,770,708 (Knoepfel et al).

SUMMARY OF THE INVENTION

One aspect of the present invention is the preparation of a hydrogel adhesive, useful for medical devices such as biomedical electrodes, from a polymer containing zwitterionic functionality.

The present invention provides a hydrophilic pressure sensitive adhesive composition comprising a zwitterionic polymer and sufficient plasticizer to render pressure sensitive adhesive, the composition. Preferably, the zwitterionic polymer is prepared from at least one zwitterionic monomer.

An advantage of the present invention is that zwitterionic functionality imparts high ionic conductivity in the adhesive both initially and after exposure to low humidity conditions which can exist in health care facilities either by natural or controlled environmental conditions.

Another aspect of the present invention is the use of adhesives of the present invention in medical devices such as biomedical electrodes, skin coverings, and transdermal delivery devices.

The present invention also provides a biomedical electrode, comprising a field of adhesive conductive medium for contacting mammalian skin and a means for electrical communication for interfacing with the adhesive conductive medium and electrical diagnostic, therapeutic, or electrosurgical instrumentation, the adhesive conductive medium adhered to the means for electrical communication and comprising an adhesive composition as described above.

The present invention also provides a mammalian skin covering comprising an adhesive layer for contacting mammalian skin and backing layer, the adhesive layer adhered to the backing layer and comprising a pressure sensitive adhesive composition as described above.

The present invention also provides a pharmaceutical delivery device comprising: an adhesive layer for contacting mammalian skin and a backing layer, the adhesive layer adhered to the backing layer and comprising a pressure sensitive adhesive composition as described above.

Use of these materials in medical devices where retained water is important for the function of the medical device can allow for reduction of the packaging required to limit "dry out" of water-containing adhesives in such devices.

Another advantage of the present invention is the use of adhesives of the present invention as a highly conductive but non-migratory matrix for iontophoretic delivery of drugs.

Embodiments of the invention described with reference to the following drawings further reveal features and advantages of the present invention.

EMBODIMENTS OF THE INVENTION

Zwitterionic Polymers

Figure 1:
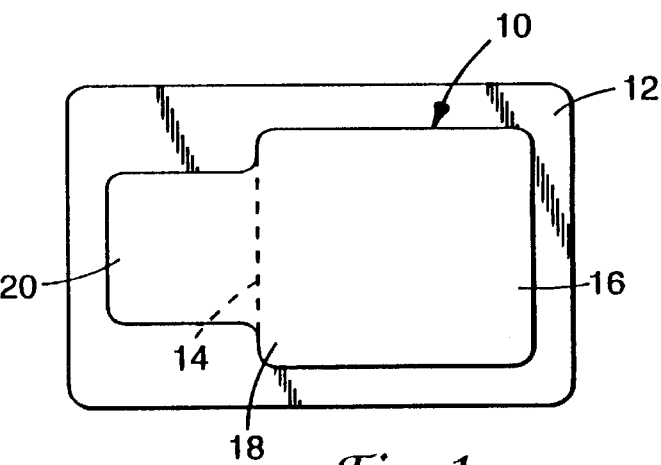
FIG. 1 is a top plan view of a biomedical electrode containing an adhesive composition of the present invention, used for diagnosis or monitoring of heart conditions of a mammalian patient.

Zwitterionic polymers useful in the practice of the present invention can be prepared using any of the methods known to those skilled in the art as disclosed in the"Polyampholytes" article described above, the disclosure of which is incorporated by reference herein. Nonlimiting examples of such methods include chemical modification of preformed polymers to make them zwitterionic or polymerization of zwitterionic monomers. Homopolymerization of zwitterionic monomer or copolymerization of a zwitterionic monomer with a hydrophilic monomer are the currently preferred methods of synthesis due to the control of molecular architecture and reduced levels of impurities that such polymerization methods afford.

Nonlimiting examples of the zwitterionic monomers are a) 3-dimethyl (methacryloyloxyethyl) ammonium propanesulfonate (SPE); b) 3-dimethyl (acryloyloxyethyl) ammonium propanesulfonate (SP-A); c) 1,1-dimethyl-1-(3-methacrylamidopropyl)-1-(3-sulfopropyl)-ammonium betaine (SPP). SPE and SPP are commercially available from Raschig Inc. SP-A is prepared following the procedure in Liaw et al., *J. Chin.Inst. Chem. Eng.* 21, 1, (1990) by reacting N,N-dimethylaminoacrylate (from Polysciences, Inc.) with 1,3-propanesultone (from Aldrich, Inc.) in acetonitrile at elevated temperature.

Other zwitterionic monomers are ammonium carboxylates such as N-(3-carboxypropyl)-N-methacrylamido-(ethyl-N,N-dimethyl) ammonium betaine and 1,1-dimethyl-1-[2-methacryloyloxyethyl]-1-[2-carboxyethyl]-ammonium betaine.

Nonlimiting examples of the hydrophilic comonomers are acrylamide (ACM); acrylic acid (AA); methacrylic acid (MAA); 2-hydroxylethyl acrylate (HEA); 2-hydroxylpropyl acrylate (HPA), N,N-dimethylaminoethyl acrylate (DMAEA), n-vinyl pyrrolidone (NVP), N,N-dimethyl acrylamide (NNDMA), and the like.

For copolymers, the amount of zwitterionic monomers can range from about 20 to about 95 weight percent of the polymer. Preferably, the amount of zwitterionic monomers can range from about 60 to about 90 weight percent of the polymer, in order to impart high ionic content to the copolymer.

The amount of hydrophilic comonomers can range from about 5 to about 80 weight percent of the polymer. Preferably, the amount of hydrophilic comonomers can range from about 10 to about 40 weight percent of the polymer, in order to provide other properties including the ability to crosslink and to be compatible with plasticizer or other additives.

Plasticizer

The plasticizer serves to increase the compliance of the zwitterionic polymers to provide adhesive properties and conformability. The plasticizer also serves to modify the tack or thumb appeal of the final polymer composition. The plasticizer can also serve as a solvent to dissolve other additives including initiators, electrolytes, and pharmacologically active components.

Using water alone as the plasticizer yields compositions with poor to moderate tack which are prone to rapid loss of moisture and a concomitant change into a leathery or glassy material when exposed to ambient conditions.

Hence useful plasticizers are those selected from the group consisting of alcohols, mixtures of alcohols, and mixtures of water and alcohols such that the mixture of plasticizer and zwitterionic polymer displays pressure sensitive tack.

Nonlimiting alcohols for the polar polymers described above include glycerin, propylene glycol, dipropylene glycol, sorbitol, 1,3-butanediol, 1,4-butanediol, trimethylol propane, and ethylene glycol and derivatives given by:

$$MO(CH_2CH_2O)_mH$$

wherein

M is selected from the group consisting of hydrogen and $C_1$ through $C_6$ alkyl, and m is an integer of about 1 to about 25.

The amount of plasticizer should be sufficient to render pressure sensitive adhesive, the composition. Preferably, the plasticizer comprises from about 30 to about 90 weight percent of the adhesive composition. Most preferably, the plasticizer comprises from about 40 to about 85 weight percent of the adhesive composition.

Optional Surfactants

Anionic, cationic, nonionic or amphoteric surfactants can optionally be used in amounts ranging from about 10 to about 80 weight percent of the final composition and preferably from about 20 to about 50 weight percent of the final composition.

The use of such surfactants improves the adhesion of the pressure sensitive adhesive electrodes to oily mammalian skin by giving the adhesive lipophilic properties. By incorporating the surfactants into the adhesive composition, the compatibility between the adhesive and the oily mammalian skin is improved.

Suitable anionic compatible surfactants include alkyl benzene sulfonates, alkyl sulfonates, olefin sulfonates, alkyl ethersulfonates, glycerol ethersulfonates, α-methyl estersulfonates, sulfonic fatty acids, alkyl sulfates, fatty alcohol ethersulfates, glycerol ethersulfates, mixed hydroxy ethersulfates, monoglyceride(ether)sulfates, fatty acid amide (ether)sulfates, sulfosuccinates, sulfosuccinamates, sulfotriglycerides, amide soaps, ether carboxylic acids, isethionates, sarcosinates, taurides, alkyl oligoglycoside sulfates and alkyl (ether)phosphates.

Suitable nonionic compatible surfactants include fatty alcohol polyglycolethers, alkyl phenylpolyglycolethers, fatty acid polyglycolesters, fatty acid amide polyglycolethers, fatty amine polyglycolethers, alkoxylated triglycerides, alk(en)yl óligoglycosides, fatty acid glucamides, polyol fatty acid esters, sugar esters, sorbitol esters and sorbitol ester ethoxylates and polysorbates.

Suitable cationic compatible surfactants include quaternary ammonium compounds and quaternized difatty acid trialkanol amine esters.

Suitable amphoteric compatible surfactants include alkyl betaines, alkyl amidobetaines, amino propionates, amino glycinates, imidazolinium betaines and sulfobetaines.

Preferred compatible surfactants may be selected from nonionic surfactants having an HLB-value of 10 to 17. Fatty alcohol polyglycolethers, sorbitol fatty acid esters, and sorbitol fatty ester ethoxylates in this HLB range are particularly preferred. As is known to those skilled in the art, the HLB-value is an acronym for the hydrophilic-lipophilic balance and indicates the extent to which a given surfactant will behave as an oil-soluble vs. a water-soluble type of emulsifier as described in Chapter 20 of *Surface Active Agents and Detergents,* Volume II, Anthony M. Schwartz, James W. Perry, and Julian Berch, Robert E. Krieger Publishing Co., Huntington, N.Y., 1977. HLB-values in this range help assure that the surfactant is soluble in the adhesive formulation and also have high enough hydrocarbon content to impart desired oil absorbancy at lower usage Optional Additives Additives can also be incorporated into the composition including non-functionalized compatible polymers.

Addition of non-functionalized compatible polymers at low levels (e.g., 10 weight percent or less) is contemplated as a means of enhancing the viscosity of the composition to impart better coatability for, for example, pattern coating of the adhesive. Suitable polymers include those that are hydrophilic and compatible in the zwitterionic polymer/plasticizer mixture including moderate and high molecular weight poly(ethylene oxide), poly(acrylic acid), poly(N-vinyl pyrrolidone), poly(vinyl alcohol), and poly(acrylamide).

Alternatively, such compatible polymers can be present in up to 40 weight percent of the formulation, serving as the primary polymer base to the adhesive with the zwitterionic polymer present in an amount ranging from about 1 to about 10 weight percent imparting the high ionic conductivity to the formulation. This alternative creates a blend of the composition of the present invention in a compatible polymer.

Biocompatible and/or Therapeutic and/or Ionically-Conductive Additives

Depending upon the use of the hydrophilic, pressure sensitive adhesive of the present invention, various biocompatible and/or therapeutic and/or ionically-conductive materials can be included in the adhesive.

For example, adhesives of the present invention can be used as conductive adhesive in a biomedical electrode with the addition of an ionically-conductive electrolyte to the adhesive. Nonlimiting examples of electrolyte include ionic salts dissolved in the adhesive to provide ionic conductivity and can include magnesium acetate, magnesium sulfate, sodium acetate, sodium chloride, lithium chloride, lithium perchlorate, sodium citrate, and preferably potassium chloride to enhance ionic conductivity of the hydrophilic pressure sensitive adhesive.

Alternatively, a redox couple such as a mixture of ferric and ferrous salts such as sulfates and gluconates can be added.

The amounts of these ionic salts present in adhesives of the present invention are relatively small, from about 0.5 to 7 percent by weight of the adhesive, and preferably about 2 to 5 weight percent. When a redox couple is used, the biomedical electrode can recover from an overload potential. U.S. Pat. No. 4,846,185 (Carim) discloses a redox couple totalling not more than about 20 percent by weight of the adhesive.

Hydrophilic, pressure sensitive adhesives of the present invention can also be used in the delivery of pharmaceuticals to or through mammalian skin, such as topical or transdermal drug delivery systems. The pharmaceutical or other active ingredient can be compounded with the adhesive after polymerization, minimizing any possible deleterious interaction of the pharmaceutical or active ingredient with the crosslinking process.

A type of therapeutic procedure both involving application of electrical current to the skin of a patient and a pharmaceutical is iontophoresis, which delivers an iontophoretically active pharmaceutical to or through mammalian skin with aid of an electrical current.

The hydrophilic, pressure sensitive adhesive can also be used in therapeutic mammalian skin coverings, such as dressings, wound closure materials, tapes, and the like. Preferably, for mammalian skin covering uses, other biologically active materials can be added to the adhesive of the present invention without deleteriously affecting the biologically active material. Nonlimiting examples of such other biologically active materials include broad spectrum antimicrobial agents where it is desired to reduce bacteria levels to minimize infection risk or treat the effects of infections at the skin or skin openings of a mammalian patient. Broad spectrum antimicrobial agents are disclosed in U.S. Pat. No. 4,310,509, which disclosure is incorporated by reference. Nonlimiting examples of other antimicrobial agents include parachlorometaxylenol; triclosan; chlorhexidine and its salts such as chlorhexidine acetate and chlorhexidine gluconate; iodine; iodophors; poly-N-vinyl pyrrolidone-iodophors; silver oxide, silver and its salts, antibiotics (e.g., neomycin, bacitracin, and polymyxin B). Antimicrobial agents can be included in the adhesive in a weight from about 0.01 percent to about 10 percent by weight of the total adhesive.

Other biocompatible and/or therapeutic materials can be added to the adhesive such as compounds to buffer the pH of the adhesive to provide a non-irritating pH for use with sensitive mammalian skin tissue or to otherwise maximize antimicrobial activity. Also, penetration enhancing agents or excipients can be added to the adhesive when the pharmaceutical or other active agent for topical or transdermal delivery so requires.

Usefulness of the Invention

Adhesive compositions of the present invention can be used in a variety of applications where pressure sensitive adhesives are industrially or commercially applied in the manufacture of tapes, adhesive substrates, and the like. Preferably, adhesive compositions of the present invention can be used in the field of health care where adhesive requirements are particularly stringent.

Because mammalian skin is a particularly difficult surface to identify and allows limited tailoring of acceptable adhesive properties, the adhesive composition of the present invention is particularly suitable for use in mammalian skin covering applications such as biocompatible medical adhesives for receipt or delivery of electrical signals at or through mammalian skin, delivery of pharmaceuticals or active agents to or through mammalian skin, or treatment of mammalian skin or mammalian skin openings against the possibilities of infection.

Biomedical Electrodes

Biomedical electrodes employing adhesive compositions of the present invention having electrolyte contained therein are useful for diagnostic (including monitoring) and therapeutic purposes. In its most basic form, a biomedical electrode comprises a conductive medium contacting mammalian skin and a means for electrical communication interacting between the conductive medium and electrical diagnostic, therapeutic, or electrosurgical equipment.

Figure 2:
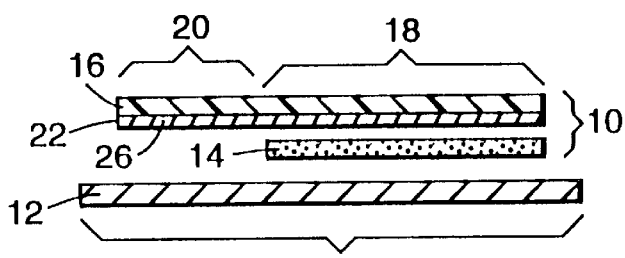
FIG. 2 is a cross-sectional view of the biomedical electrode of FIG. 1.

FIGS. 1 and 2 show either a disposable diagnostic electrocardiogram (ECG or EKG) or a transcutaneous electrical nerve stimulation (TENS) electrode 10 on a release liner 12. Electrode 10 includes a field 14 of a biocompatible and adhesive conductive medium for contacting mammalian skin of a patient upon removal of protective release liner 12. Electrode 10 includes means for electrical communication 16 comprising a conductor member having a conductive interface portion 18 contacting field 14 of conductive medium and a tab portion 20 extending beyond field 14 of conductive medium for mechanical and electrical contact with electrical instrumentation (not shown). Means 16 for electrical communication includes a conductive layer 26 coated on at least the side 22 contacting field 14 of conductive medium.

It is foreseen that a typical conductor member 16 will comprise a strip of material having a thickness of about 0.05–0.2 millimeters, such as polyester film and have a coating 26 on side 22 of silver/silver chloride of about 2.5–12 micrometers, and preferably about 5 micrometers thick thereon. Presently preferred for conductor member 16 are polyester films commercially available as Scotchpak™ brand film from Minnesota Mining and Manufacturing Company of St. Paul, Minn. or "Melinex" 505-300, 329, or 339 brand film from ICI Americas of Hopewell, Va. coated with a silver/silver chloride ink commercially available as "R-300" ink from Ercon, Inc. of Waltham, Mass. A TENS conductor member 16 can be made of a nonwoven web, such as a web of polyester/cellulose fibers commercially available as "Manniweb" material from Lydall, Inc. of Troy, N.Y. and have a carbon ink layer 26 commercially available as "SS24363" ink from Acheson Colloids Company of Port Huron, Mich. on side 22 thereof. To enhance mechanical contact between an electrode clip (not shown) and conductor member 16, an adhesively-backed polyethylene tape can be applied to tab portion 20 on the side opposite side 22 having the conductive coating 26. A surgical tape commercially available from 3M Company as "Blenderm" tape can be employed for this purpose.

Alternatively, conductor member can be a multi-layered construction of a nonconductive, flexible polymeric film having a sulfur-reactive surface, a metallic layer deposited on and interacting with the surface and an optional metallic halide layer, according to the disclosure of PCT Publication WO 94/026950, the disclosure of which is incorporated by reference herein. The conductive interface portion 18 of member 16 comprises a metallic layer deposited on a sulfur-reactive surface on at least the side of polymeric film substrate facing field 14 of the conductive medium and the optional metallic halide layer coated on the metallic layer and contacting field 14. Because depolarizing is not needed for the mechanical and electrical contact with electrical equipment, the optional metallic halide layer does not need to extend to tab portion 20.

Alternatively, conductor member 16 can be a multi-layered construction of a nonconductive, flexible polymeric film, an electrically conductive layer, and a thin, conformable depolarizing layer of inorganic oxide, preferably manganese dioxide. Alternatively, conductor member 16 is a multi-layered construction of film with electrically conductive and depolarizing layers blended together. Both of these alternative embodiments can be constructed according to the disclosure of PCT International Patent Publication WO 95/20350, the disclosure of which is incorporated by reference herein. The conductive interface portion of member comprises an electrically conductive layer coated on at least the side of polymeric film facing field 14 of conductive medium and the thin, depolarizing layer coated on the electrically conductive layer and contacting field 14. Because depolarizing is not needed for the mechanical and electrical contact with electrical equipment, the depolarizing layer does not need to extend to tab portion 20.

Non-limiting examples of biomedical electrodes which can use adhesive compositions of the present invention, either as conductive or non-conductive adhesive fields include electrodes disclosed in U.S. Pat. Nos. 4,524,087; 4,539,996; 4,554,924; 4,848,353 (all Engel); 4,846,185 (Carim); 4,771,783 (Roberts); 4,715,382 (Strand); 5,012,810 (Strand et al.); and 5,133,356 (Bryan et al.), the disclosures of which are incorporated by reference herein.

In some instances, the means for electrical communication can be an electrically conductive tab extending from the periphery of the biomedical electrodes such as that seen in U.S. Pat. No. 4,848,353 or can be a conductor member extending through a slit or seam in an insulating backing member, such as that seen in U.S. Pat. No. 5,012,810. Otherwise, the means for electrical communication can be an eyelet or other snap-type connector such as that disclosed in U.S. Pat. No. 4,846,185. Further, the means for electrical communication can be a lead wire such as that seen in U.S. Pat. No. 4,771,783. Regardless of the type of means for electrical communication employed, an adhesive composition of the present invention, containing an electrolyte, can reside as a field of conductive adhesive on a biomedical electrode for diagnostic (including monitoring), therapeutic, or electrosurgical purposes.

Another type of diagnostic procedure which can employ a biomedical electrode of the present invention is the longer term monitoring of electrical wave patterns of the heart of a patient to detect patterns of abnormality. A preferred biomedical electrode structure is disclosed in U.S. Pat. No. 5,012,810 (Strand et al.) which is incorporated by reference. The adhesive of the present invention can be used as the ionically conductive medium in any of the embodiments shown therein. Preferably, the adhesive of the present invention is used as the field of conductive adhesive in the biomedical electrode of the embodiment shown in FIGS. 2, 3, and 4 of U.S. Pat. No. 5,012,810.

Figure 3:
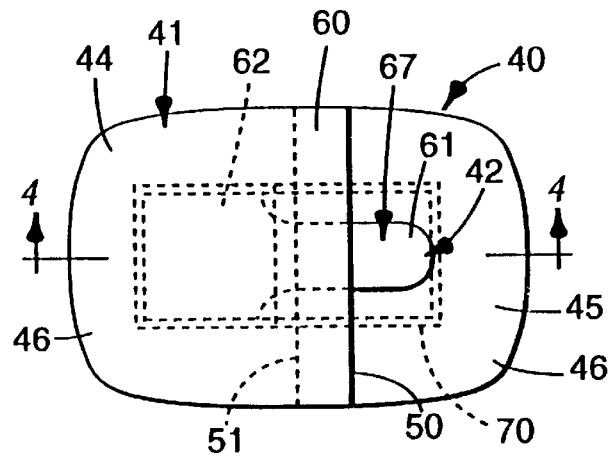
FIG. 3 is a top plan view of a monitoring biomedical electrode containing an adhesive composition of the present invention, used for longer term diagnosis or monitoring of heart conditions.
Figure 4:
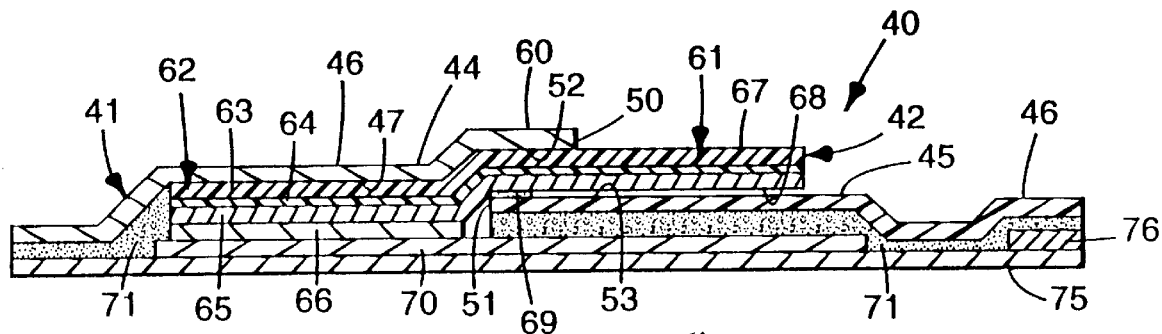
FIG. 4 is a cross-sectional view of the monitoring biomedical electrode of FIG. 3.

FIGS. 3 and 4 substantially correspond to FIGS. 2 and 3, respectively, of U.S. Pat. No. 5,012,810. Electrode 40 includes an insulator construction 41, and a conductor member 42.

The insulator construction 41 includes first and second sections 44 and 45 which, together, define opposite sides 46 and 47 of the insulator construction 41. As seen in FIG. 3, each section 44 and 45 includes an elongate edge portion 50 and 51, respectively. The edge portions 50 and 51 each include a border portion 52 and 53, respectively, which comprise a peripheral portion of each section 44 and 45, respectively, and extending along edges 50 and 51, respectively. In that manner, sections 44 and 45 are oriented to extend substantially parallel to one another, with edge portions 50 and 51 overlapping one another such that border portions 52 and 53 overlap. A seam 60 is created between edge portions 50 and 51. "Substantially parallel" does not mean that the sections 44 and 45 are necessarily precisely parallel. They may be out of precise coplanar alignment due, for example, to the thickness of the conductor member 42.

Conductor member 42 is substantially similar to biomedical electrical conductor 16 described above, having a tab portion 61 corresponding to tab portion 20 described above and a pad portion 62 corresponding to conductive interface portion 18 described above. Like biomedical electrical conductor member 16, conductor member 42 can be any of the embodiments disclosed above. In this embodiment, conductor member 42 is a multi-layered construction of a nonconductive, flexible organic polymer substrate 63 having an organosulfur surface 64, a metallic layer 65 adhered thereto, and, optionally, a metallic halide layer 66, produced according to the disclosure of PCT Patent Publication WO 94/26950.

The pad portion 62 of member 42 comprises the portion of the metallic film facing field 70 of conductive adhesive, optionally with metallic halide layer 66 contacting field 70. Because depolarizing is not needed for the mechanical and electrical contact with electrical equipment, metallic halide layer 66 need not extend to tab portion 61. Optionally, an adhesively-backed polyethylene tape can be applied to tab portion 61 in the same manner as that for the embodiment of FIGS. 1 and 2 in order to enhance mechanical contact.

In general, electrode 40 is constructed such that tab portion 61 of conductor member 42 projects through seam 60 and over a portion of surface or side 46. As a result, as seen in FIGS. 3 and 4 pad portion 62 of conductor member 42 is positioned on one side 46 of insulator construction 41, and the tab portion 61 of conductor member 42 is positioned on an opposite side 46 of insulator construction 41. It will be understood that except where tab portion 61 extends through seam 60, the seam may be sealed by means of an adhesive or the like.

As seen in FIG. 4, lower surface 68 of tab portion 61 is shown adhered in position to section 45, by means of double-stick tape strip 69. That is, adhesion in FIG. 4 between the tab portion 61 and section 45 is by means of adhesive 69 underneath tab portion 61.

In FIG. 4, a field 70 of conductive adhesive of the present invention is shown positioned generally underneath conductive member 42. Optionally, field 70 of conductive adhesive will be surrounded by a field 71 of biocompatible skin adhesive also applied to insulator construction 41 the side thereof having pad portion 62 thereon.

In FIG. 4, a layer of release liner 75 is shown positioned against that side of electrode 40 which has optional skin adhesive 71, conductive adhesive 70 and pad portion 62 thereon. Optionally as shown in FIG. 4, a spacer 76 or tab 76 can be positioned between release liner 75 and a portion of insulator construction 41, to facilitate the separation.

A variety of release liners 75 may be utilized; for example, a liner comprising a polymer such as a polyester or polypropylene material, coated with a silicone release type coating which is readily separable from the skin adhesive and conductive adhesive.

A variety of materials may be utilized to form the sections 44 and 45 of the insulator construction 41. In general, a flexible material is preferred which will be comfortable to the user, and is relatively strong and thin. Preferred materials are polymer foams, especially polyethylene foams, non-woven pads, especially polyester non-wovens, various types of paper, and transparent films. Nonlimiting examples of transparent films include polyester film such as a "Melinex" polyester film commercially available from ICI Americas, Hopewell, Va. having a thickness of 0.05 mm and a surgical tape commercially available from 3M Company as "Transpore" unembossed tape.

The most preferred materials are non-woven pads made from melt blown polyurethane fiber, which exhibit exceptional flexibility, stretch recovery and breathability. Melt blown polyurethane materials usable in insulator construction 41 in electrodes according to the present invention are generally described in European Patent Publication 0 341 875 (Meyer) and corresponding U.S. Pat. No 5,230,701 (Meyer et al.), incorporated herein by reference.

Optionally the insulator construction has a skin adhesive on its surface contacting the remainder of the electrode 40.

Preferred web materials (melt blown polyurethanes) for use in insulator construction 41 have a web basis weight of about 60–140 g/m$^2$ (preferably about 120 g/m$^2$). Such materials have an appropriate tensile strength and moisture vapor transmission rate. A preferred moisture vapor transmission rate is about 500–3000 grams water/m$^2$/24 hours (preferably 500–1500 grams water/m$^2$24 hours) when tested according to ASTM E96-80 at 21° C. and 50% relative humidity. An advantage to such materials is that webs formed from them can be made which exhibit good elasticity and stretch recovery. This means that the electrode can stretch well, in all directions, with movement of the subject, without loss of electrode integrity and/or failure of the seal provided by the skin adhesive. Material with a stretch recovery of at least about 85%, in all directions, after stretch of 50% is preferred.

It will be understood that a variety of dimensions may be utilized for the biomedical electrode disclosed herein. Generally an insulator construction of about 3.5–4.5 cm by 5.5–10 cm will be quite suitable for typical foreseen applications.

It will also be understood that a variety of materials may be utilized as the skin adhesive. Typically, acrylate ester adhesives will be preferred. Acrylate ester copolymer adhesives are particularly preferred. Such material are generally described in U.S. Pat. Nos. 2,973,826; Re 24,906; Re 33,353; 3,389,827; 4,112,213; 4,310,509; 4,323,557; 4,732, 808; 4,917,928; 4,917,929; and European Patent Publication 0 051 935, all incorporated herein by reference.

In particular, an adhesive copolymer having from about 95 to about 97 weight percent isooctyl acrylate and from about 5 to about 3 percent acrylamide and having an inherent viscosity of 1.1–1.25 dl/g is presently preferred.

Adhesive useful for adhesive 69 can be any of the acrylate ester adhesives described above in double stick tape form. A presently preferred adhesive is the same adhesive as presently preferred for the skin adhesive except having an inherent viscosity of about 1.3–1.45 dl/g.

It will be understood that the dimensions of the various layers, and their conformation during association, are shown somewhat exaggerated in FIG. 4, to facilitate an understanding of the construction. In general, an overall substantially flat appearance with only a very minor "s" type bend in the conductive member 42 is accommodated by the arrangement, despite the multi-layered construction of member 42.

Figure 5:
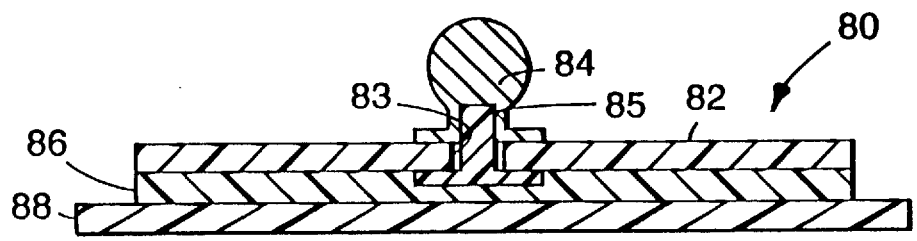
FIG. 5 is a cross-sectional view of another monitoring biomedical electrode containing an adhesive compositon of the present invention and a stud connector.

Another biomedical electrode construction is shown in FIG. 5 in cross-section. Electrode 80 has a nonconductive backing 82 having an opening 83 covered by snap 84 though which stud or eyelet 85 protrudes. The snap 84 is secured to eyelet 85 to provide a point of electrical connection to electrical instrumentation. Covering eyelet 84 and backing 82 is a field 86 of the adhesive of the present invention. A release liner 88 protects the PSA field 86 prior to use. Backing 82 can be made of the same or similar materials as insulator construction 41. Eyelet 85 can be a plastic, metallic plated eyelet (such as an ABS plastic eyelet silver-plated and chlorided and commercially available from Micron Products of Fitchburg, Mass.). Snap 84 can be a metallic snap (such as stainless steel eyelet No. 304 commercially available from Eyelets for Industry of Thomason, Conn.).

Other examples of biomedical electrodes which can use the present invention as a conductive adhesive include electrodes disclosed in U.S. Pat. No. 4,527,087; 4,539,996; 4,554,924; 4,848,353 (all Engel); 4,846,185 (Carim); 4,771, 783 (Roberts); 4,715,382 (Strand); 5,133,356 (Bryan et al.), the disclosures of which are incorporated by reference herein. Methods of making such electrodes are disclosed in such patents, except that adhesive of the present invention can be substituted for the field of conductive adhesive. Among these various electrode constructions is an electrode construction particularly preferred as that shown in FIGS. 4 and 5 of U.S. Pat. No. 4,848,353 (Engel) in which the electrically conductive adhesive 36 is replaced by the adhesive of the present invention, .

When used for diagnostic EKG procedures, electrodes shown in FIGS. 1 and 2 or those electrodes shown in U.S.

Pat. No. 4,539,996 are preferred. When used for monitoring electrocardiogram (ECG) procedures, electrodes shown in FIGS. 3 and 4 and those disclosed in U.S. Patent Nos. 4,539,996, 4,848,353, 5,012,810 and 5,133,356 are preferred.

In some instances, the biomedical electrical conductor can be an electrically conductive tab extending from the periphery of the biomedical electrodes such as that seen in U.S. Pat. No. 4,848,353 or can be a conductor member extending through a slit or seam in a insulating backing member, such as that seen in U.S. Patent No. 5,012,810. Otherwise, the means for electrical communication can be an eyelet or other snap-type connector such as that disclosed in U.S. Pat. No. 4,846,185. Alternatively, an electrically conductive tab such as that seen in U.S. Pat. No. 5,012,810 can have an eyelet or other snap-type connector secured thereto.

Medical Skin Coverings

Medical skin coverings employing adhesive compositions of the present invention, optionally having antimicrobial and other biologically active agents contained therein, are useful for treatment of mammalian skin or mammalian skin openings, preferably against the possibility of infection and also for the transmission of moisture vapor and exudate from skin.

Figure 6:
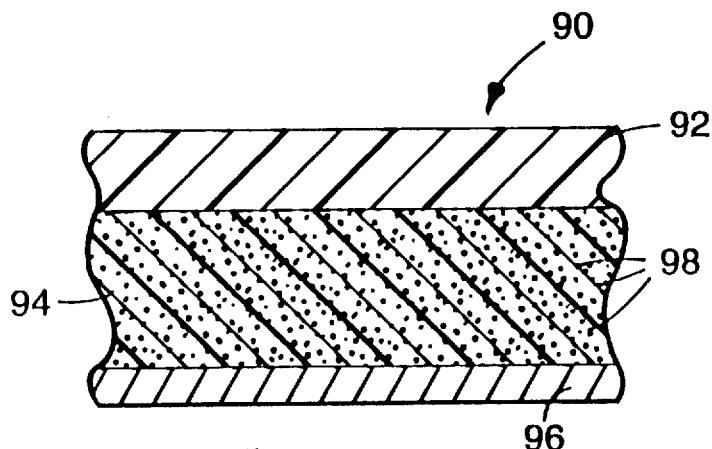
FIG. 6 is a sectional view of a medical mammalian skin covering containing adhesive composition of the present invention.

FIG. 6 shows a sectional view of a medical skin covering 90 having a backing material 92, a layer 94 of adhesive of the present invention coated on backing material 92, and protected until use by a release liner 96. Preferably, antimicrobial 98 is contained in layer 94 by adding agent 98 prior to coating on backing material 92. Alternatively, layer 94 can be used as a caulkable sealant according to U.S. Pat. No. 4,931,282 (Asmus et al.), the disclosure of which is incorporated by reference herein.

For use, the release liner 96 is removed and the layer 94 of adhesive of the present invention can be applied to the skin of the patient as a part of a medical tape, a wound dressing, a bandage of general medicinal utility, or other medical device having water absorbing properties.

The adhesive layer 94 may be coated on a layer of backing material 92 selected from any of several backing materials having a high moisture vapor transmission rate for use as medical tapes, dressings, bandages, and the like. Suitable backing materials include those disclosed in U.S. Pat. Nos. 3,645,835 and 4,595,001, the disclosures of which are incorporated by reference. Other examples of a variety of films commercially available as extrudable polymers include "Hytrel® 4056" and "Hytre® 3548" branded polyester elastomers available from E.I. DuPont de Nemours and Company of Wilmington, Del., "Estane" branded polyurethanes available from B. F. Goodrich of Cleveland, Ohio or "Q-thane" branded polyurethanes available from K. J. Quinn & Co. of Malden, Mass.

The layer 94 of adhesive of the invention combined with a layer 92 of suitable backing material can be used as a dressing.

Adhesive compositions of the present invention can be used as discrete gel particles dispersed in a continuous pressure-sensitive adhesive matrix to form a two phase composite usefull in medical applications, as described in U.S. Pat. No. 5,270,358, the disclosure of which is incorporated by reference herein.

The adhesive layer 94 can be coated on the backing layer 92 by a variety of processes, including, direct coating, lamination, and hot lamination. The release liner 96 can thereafter be applied using direct coating, lamination, and hot lamination.

The methods of lamination and hot lamination involve the application of pressure, or heat and pressure, respectively, on the layer of adhesive layer 94 to the backing material layer 92. The temperature for hot lamination ranges from about 50° to about 250° C., and the pressures applied to both lamination and hot lamination range from 0.1 Kg/cm$^2$ to about 50 Kg/cm$^2$.

Pharmaceutical Delivery Devices

Pharmaceutical delivery devices employing hydrophilic, pressure-sensitive adhesive compositions of the present invention, optionally having a topical, transdermal, or iontophoretic therapeutic agent and excipients, solvents, or penetration enhancing agents contained therein, are useful for delivery of pharmaceuticals or other active agents to or through mammalian skin.

Figure 7:
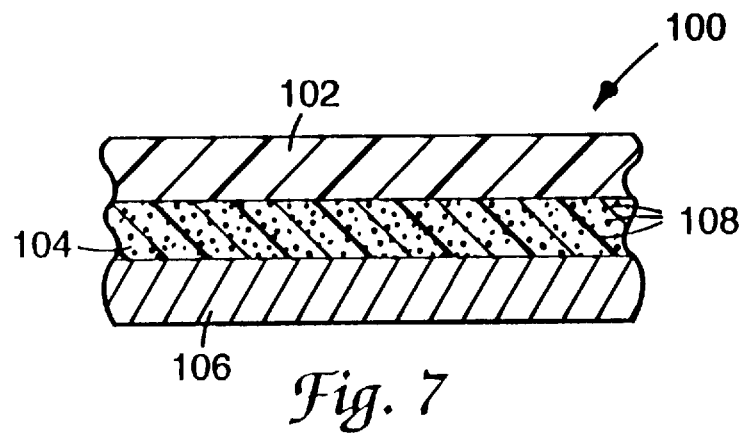
FIG. 7 is a sectional view of a pharmaceutical delivery device containing an adhesive composition of the present invention.

FIG. 7 shows a sectional view of a transdermal or topical drug delivery device 100 having a backing layer 102, a layer 104 containing adhesive of the present invention coated thereon and protected by a release liner 106. Other layers can be present between layer 102 and layer 104 to house pharmaceuticals or other therapeutic agents. Otherwise, as shown in FIG. 7, pharmaceutical and other agents 108 are dispersed in adhesive layer 104.

The backing layer 102 can be any backing material known to those skilled in the art and useful for drug delivery devices. Non-limiting examples of such backing materials are polyethylene, ethylene-vinyl acetate copolymer, polyethylene-aluminum-polyethylene composites, and ScotchPak™ brand backings commercially available from Minnesota Mining and Manufacturing Company of St. Paul, Minn.

The release liner 106 can be any release liner material known to those skilled in the art. Non-limiting examples of such release liners commercially available include siliconized polyethylene terephthalate films commercially available from H. P. Smith Co. and fluoropolymer coated polyester films commercially available from 3M under the brand ScotchPak™ release liners.

The therapeutic agent 108 can be any therapeutically active material known to those skilled in the art and approved for delivery topically to or transdermally or iontophoretically through the skin of a patient. Non-limiting examples of therapeutic agents useful in transdermal delivery devices are any active drug or salts of those drugs, used in topical or transdermal applications, or growth factors for use in enhancing wound healing. Other therapeutic agents identified as drugs or pharmacologically active agents are disclosed in U.S. Patent Nos. 4,849,224 and 4,855,294, and PCT Patent Publication WO 89/07951.

Excipients or penetration enhancing agents are also known to those skilled in the art. Non-limiting examples of penetration enhancing agents include ethanol, methyl laurate, oleic acid, isopropyl myristate, and glycerol monolaurate. Other penetration enhancing agents known to those skilled in the art are disclosed in U.S. Patent Nos. 4,849,224; and 4,855,294 and PCT Patent Publication WO 89/07951.

The method of manufacturing a transdermal delivery device depends on its construction.

The drug delivery device 100 shown in FIG. 7 can be prepared using the following general method. A solution is prepared by dissolving the therapeutic agent 108 and such optional excipients as are desired in a suitable solvent and mixed into the precursor prior to forming the composition, during the formation of the composition, or directly into the already formed composition. The resulting loaded adhesive composition is coated on the backing layer 102. A release liner 106 is applied to cover loaded adhesive layer 104.

Other aspects of the present invention are identified in the following examples.

Method of Preparation

The zwitterion-containing copolymers can be prepared, and for the following examples were prepared, by conventional solution polymerization in a 1-liter, jacketed, cylindrical reaction flask equipped with a four-neck flask head. The head was fitted with a glass stirring rod with tilted blades, a reflux condenser, a thermometer, and a nitrogen inlet tube. For a typical preparation, radical initiator potassium persulfate (KPS=$K_2S_2O_8$) (1 wt % relative to monomers) was used to initiate the polymerization. The solution was stirred at 300 rpm, and the polymerization was conducted for six hours at 70° C. under nitrogen atmosphere. Potassium chloride (KCl) salt can be added into the polymers during or after the polymerization.

EXAMPLES 1–3

The solubility of zwitterionic polymers in water depends on several factors: content of zwitterion monomer, total monomer loading, and ionic strength of the medium. Examples illustrate the syntheses of the subject zwitterion homo- or copolymers, which are then formulated with a plasticizer/tackifier and potassium chloride to afford conductive hydrogels.

Poly (SPE-co-HEA) (Example 1): SPE (289 g), HEA (30 g), and D.I. water (742 g) were charged to a 1-liter, jacketed reactor. The reaction mixture was stirred at 300 rpm, and purged with $N_2$ at 70° C. for 15 min. KPS (3.18 g) was then added into the mixture to initiate the polymerization. The reaction proceeded for 6 hr. The viscosity of the solution gradually increased during the polymerization. At the end of polymerization, the polymer solution was water-transparent and had a viscosity of 20,600 cps.

The homopolymer of SPE (Example 2) was synthesized by using the polymerization method of Example 1. This homopolymer solution had opaque appearance. Upon adding trace amount of salt, the solution becomes transparent.

Poly(SPE-co-HPA) (Example 3) was synthesized by using the polymerization method of Example 1, except that HPA replaced HEA.

EXAMPLES 4–6

The incorporation of carboxyl functional groups allowed for the introduction of UV crosslinkable functionalities. For example, the modification of such polymers with glycidyl methacrylate produced polymers which are UV curable according to the disclosure of copending, coassigned patent application PCT US 95/17079 (Attorney Docket No. 51537PCT4A), the disclosure of which is incorporated by reference herein. SPE was polymerized with MAA at 30% solids. The polymerizations were conducted in water as described below.

Monomers, SPE and MAA, were added into a 1-liter, water-jacketed, glass reactor. The solution was stirred and purged with $N_2$ for 15 min. To this solution was added 1 wt % KPS (relative to monomers) and the temperature was raised to 70° C. The polymerization proceeded for 6 hr. The specifics of the formulations are shown in the following Table 1.

TABLE 1

| Example | SPE (g) | MAA (g) | KPS (g) | Water (g) |
|---|---|---|---|---|
| 4 | 83.80 | 8.61 | 0.93 | 228 |
| 5 | 75.42 | 2.58 | 0.78 | 192.63 |
| 6 | 89.39 | 6.89 | 0.96 | 237.35 |

EXAMPLES 7–12

The resulting polymers from Examples 1–6 were used in generating the conductive adhesives are characterized below in Table 2. Viscosity was measured at shear rate of 0.0731 (1/s) using a C25 cup and bob method and a Bohlin VOR Rheometer.

TABLE 2

| Example | Polymer Viscosity | Composition | Mol. Ratio | % Solids in Water | Viscosity |
|---|---|---|---|---|---|
| 7 | 1 | Poly(SPE-co-HEA) | 70/30 | 30% | high |
| 8 | 2 | Poly(SPE) |  | 30% | low |
| 9 | 3 | Poly(SPE-co-HPA) | 70/30 | 20% | low |
| 10 | 4 | Poly(SPE-co-MAA) | 75/25 | 29% | 3.35 Pas |
| 11 | 5 | Poly(SPE-co-MAA) | 90/10 | 29% | 1.08 Pas |
| 12 | 6 | Poly(SPE-co-MAA) | 80/20 | 29% | 1.22 Pas |

Samples of adhesive from Examples 7–12 were formulated with glycerin and aqueous potassium chloride, knife coated 40 mil wet onto polyester film coated with Ercon R301 silver/silver chloride ink (commercially available from Ercon, Inc. of Waltham, Mass.), dried in a 93° C. oven for 20 minutes (7A–B, 8A–C, and 9A–C) or 45 minutes (10A–B, 11A–B, and 12A–C) and assessed for tack after cooling. For Examples 7A–B, 8A–C, and 9A–C, the coatings were then rehydrated by placing in a humidity chamber (60% RH, 24° C.) overnight and the tack reassessed. Formulations and results are shown below in Table 3.

TABLE 3

| Ex. | Polymer (g) | Glycerin (g) | 25% KCl (g) | $H_2O$ (g) | Initial Tack | After Humidity Conditioning |
|---|---|---|---|---|---|---|
| 7A | 10 | 3 | 0.48 | 5 | nice tack/no residue | thick honey |
| 7B | 10 | 6 | 0.72 | 5 | soft/residue | syrup |
| 8A | 10 | 0 | 0.24 | 0 | tack free/brittle | tack free/flex |
| 8B | 10 | 3 | 0.48 | 0 | similar to 7A | similar to 7A |
| 8C | 10 | 6 | 0.72 | 0 | similar to 7B | similar to 7B |
| 9A | 10 | 0 | 0.16 | 0 | similar to 8A | similar to 8A |
| 9B | 10 | 2 | 0.32 | 0 | similar to 7A | similar to 7A |
| 9C | 10 | 4 | 0.48 | 0 | similar to 7B | similar to 7B |
| 10A | 10 | 3 | 0.5 | 0 | moderate tack |  |
| 10B | 10 | 6 | 0.7 | 0 | good tack/residue |  |
| 11A | 10 | 3 | 0.5 | 0 | good tack |  |
| 11B | 10 | 6 | 0.7 | 0 | thick honey |  |
| 12A | 10 | 3 | 0.5 | 0 | moderate tack |  |
| 12B | 10 | 6 | 0.7 | 0 | honey |  |

As can be seen from these results, on drying, a one-to-one ratio of polymer solids to glycerin gave better tack and cohesion than a one-to-two ratio, although cohesive strength was lost under high humidity conditions.

EXAMPLE 13 AND COMPARATIVE EXAMPLE A

A study was conducted comparing the dryout characteristics of a conductive adhesive based on zwitterionic polymer (Example 7A) to a similar formulation made with poly(acrylamide)—a very polar but non-ionic polymer.

Example 13 was prepared by taking 20 g of Example 7 and formulating it with 6 g glycerin, 0.96 g 25% aqueous KCl, and 7.3 g water (added to give a similar percent solids to that of the poly(acrylamide) formulation).

Comparative Example A was prepared by taking 27.3 g of Callaway 4608 (a moderate molecular weight 92/8 acrylamide/acrylic acid copolymer at 22% solids in water available from Callaway Chemical, Columbus, Ga.) and formulating it with 6 g glycerin and 0.96 g 25% aqueous KCl.

After mixing overnight, both homogeneous solutions were knife coated at 40 mil wet thickness onto a 3 mil thick polyester film coated with Ercon R301 silver/silver chloride ink. After drying for 30 minutes in a 93° C. forced air oven, tab-style electrodes with a 2.54 cm×2.54 cm conductive adhesive area were cut and back to back electricals as specified by the Association of the Advancement of Medical Instrumentation (AAMI) run on an Xtratec electrode tester, commercially available from Xtratec, Inc. of Lenexa, Kans.

The impedance for the zwitterionic adhesive (Example 13) averaged 1475 ohms for the two pairs tested, while those of the acrylamide adhesive of Comparative Example A were both overrange at greater than 4,000 ohms.

A portion of each sheet was allowed to rehydrate by laying out open-faced in ambient conditions (21° F., 55 to 63% RH) for two days. After this, the zwitterionic adhesive of Example 13 was soft and tacky with moderate cohesive strength and electrodes give a back to back impedance of less than 10 ohms. The acrylamide adhesive of Comparative Example A was firm and tacky with a back to back impedance of 350 ohms.

Portions of the oven-dried films were also placed in a desiccator over Drierite-brand calcium sulfate desiccant to further remove water. After two weeks AAMI "electricals" were run again finding an average of 1160 ohms for the two pairs of now low tack zwitterionic adhesive of Example 13 tested, while the very low tack acrylamide adhesive of Comparative Example A was still overrange. This relatively low impedance even after exposure to very low humidity conditions can offer promise for use in an electrode construction that can eliminate the expensive barrier packaging currently used in biomedical electrodes.

The loss of cohesive strength under high humidity conditions is due to water uptake and overplasticization of this linear polymer. Three approaches were taken to improve cohesive strength as described in the following examples.

EXAMPLES 14 and 15

The zwitterionic polymers of Examples 7 and 8 were added at low levels to a Solid State adhesive formulation to form Examples 14 and 15, respectively. The Solid State adhesive was based on poly(N-vinyl pyrrolidone) which is crosslinked in the dry state by exposure to gamma irradiation, then compounded with humectant, salt, and water; coated; and dried as described in U.S. Pat. No. 5,276,079 (Duan et al.).

Specifically, 2 g of magnesium acetate was dissolved in a mixture of 75 g glycerin and between 103.5 and 114 g deionized water. 23 g of the gamma crosslinked PVP was sifted in slowly to the well stirred solution, and stirring continued for 10 to 50 minutes. 15.5 g aqueous solution (4.7 g of solids) of either 70/30 SPE/HEA copolymer of Example 7 or SPE homopolymer of Example 8 were added and stirring continued an additional hour to hour and a half.

The resulting homogeneous solutions were poured into a patient plate sized well of 129 $cm^2$ (20 sq. in.) generated by die cutting it out of 0.95 mm (38 mil.) foam backing and adhering the border to an aluminum cake pan. After drying overnight open-faced at room temperature, a sweep of conductivity versus frequency was taken on these soft, tacky gels using impedance testing of the conductive adhesive laminated with 129 $cm^2$ (20 sq. in.) die cut aluminum foil and tested on a Schlumberger S1 1260 Impedance Gain-Phase Analyzer with a Schlumberger Solarton 12603 in-circuit test module. Impedances for both conductive adhesives of Examples 14 and 15 are in the 3 ohm region at frequencies above about 5,000 Hertz, which remains essentially constant after about 18 days at room temperature.

EXAMPLES 16–18

The 90/10 SPE/MAA copolymer of Example 11 was functionalized with glycidyl methacrylate, applying the technology described in copending, coassigned patent application PCT US 96/17079 (Attorney Docket 51537PCT4A). Into a 500 mL 3-necked round bottomed flask equipped with mechanical stirrer and thermometer was charged 100 g of the zwitterionic polymer of Example 11 (30 g polymer contained). The pH was adjusted from 3 up to about 5 by addition of a low level of 20% NaOH. The resulting solution was heated to 95° C. for 1 hour to destroy residual thermal initiator. 0.02 g mono-methylether of hydroquinone (MEHQ) was added followed by 0.36 g (2.5 mmole) glycidyl methacrylate to functionalize the polymer every 12,000 mw with a pendant methacrylate moiety (i.e., on average with 1 methacrylate moiety for 12,000 in molecular weight of the backbone). After stirring well, half of the solution was removed and further 0.09 g (0.6 mmole) GMA was added to the balance yielding average functionalization for every 8,000 mw of backbone. A 2.5 g portion of each the 8,000 and 12,000 functionalized materials were formulated with 2.5 g glycerin, 0.4 g 25% aqueous KCl, and 0.01 g Darocur™ 1173 photoinitiator commercially available from Ciba Geigy of Hawthorne N.Y. The resulting solutions cured against a polyester film coated with Ercon R301 ink by exposing to UV irradiation from a Fusion lamp-three passes at 6 m/min. (20 ft/min.) (about 600 mj/sq cm). The resulting adhesive from the 12,000 mw material of Example 16 was very soft with low cohesive strength, while that from the 8,000 mw material was firm and dry with low tack.

A further formulation (Example 18), prepared by blending equal portions of the 8,000 mw and 12,000 mw materials gave good tack adhesives on cure, with electrodes having back to back impedances of 140 ohms. A portion placed in the desiccator over Drierite for one week yielded a firmer more aggressive adhesive with a back to back impedance of 1330 ohms.

EXAMPLE 19

The 80/20 SPE/MAA copolymer was neutralized and crosslinked with zirconium (+4) valency cation as follows.

To 25.3 g of the zwitterionic polymer of Example 12 was charged 1.1 g 20% aqueous NaOH to neutralize the acid giving a pH of 7. 30 g of glycerin and 2.4 g of 25% aqueous KCl was charged followed by portionwise addition of a 10% aqueous solution of $Zr(SO_4)_2 \cdot 4H_2O$ with stirring. When 4.1 g was added a moderate gel occurred. A portion was transferred to an Ercon R301 ink coated polyester film, a siliconized release liner placed over it, and the gel pressed to a uniform 0.63 mm thickness using a roller, and after sitting overnight back to back electrical testing was run on electrodes cut from the somewhat firm moderate tack adhesive yielding impedances of 90 ohms.

EXAMPLE 20 AND COMPARATIVE EXAMPLE B

Electrodes were prepared from zirconium (+4) valency crosslinked neutralized 80/20 SPE/MAA, exposed to low humidity conditions, (Example 20) and tested for back to back and skin impedance and compared to electrodes prepared from Callaway 4608 (Comparative Example B) and treated in similar fashion.

To 25.5 g of the zwitterionic polymer of Example 12 was charged 1.0 g 20% aqueous NaOH to neutralize the acid giving a pH of 7. 34.8 g of glycerin, 5.2 g of 25% aqueous KCl, and 14.9 g water was charged followed by 2 g of 10% aqueous $Zr(SO_4)_2 \cdot 4H_2O$. The resulting lightly gelled 54% solids solution was coated onto an Ercon R301 ink coated polyester film at 1.5 mm thick and dried in a forced air oven for 2 hours at 93° C. followed by 3 hours at 121° C. The resulting coated sheets were then placed in a desiccator over Drierite-brand calcium sulfate desiccant for three days.

Comparative electrodes with a polyacrylamide base were similarly prepared by mixing 50 g Callaway 4608 (a moderate molecular weight 92/8 acrylamide/acrylic acid copolymer at 22% solids in water available from Callaway Chemical, Columbus, Ga.) with 37.5 g glycerin and 6 g 25% aqueous KCl and adding 2 g 10% aqueous $Zr(SO_4)_2 \cdot 4H_2O$, coating and drying as above.

After this low humidity conditioning, back to back impedance measurements were done on 2.5 cm by 2.5 cm square electrodes using the Xtratec tester as described above, finding 385 ohms for the zwitterionic based adhesive of Example 20 and 3360 ohms for the polyacrylamide based adhesive of Comparative Example B.

Skin impedance measurements at 10 Hz. were done for these electrodes using a Prep-Check brand electrode impedance meter Model EIM105 from General Devices, Ridgefield N.J. A site was abraded with 3M OneStep skin prep just above the inner elbow on the left arm of two male subjects and a Red Dot 2237 monitoring electrode (3M Company) was placed on that site as a control. One leadwire of the impedance meter was attached to that control electrode and the other leadwire attached to the tab of 2.5 cm by 2.5 cm electrodes cut out of the coated sheet material. These electrodes were then firmly pressed onto the inner forearm and the reading from the meter taken after 1 minute of application.

Two electrodes of each type were placed on each subject, as were two Red Dot 2237 electrodes for comparison. The average impedance for the zwitterionic based electrode of Example 20 was 195 kohms which is comparable to the Red Dot 2237 electrode at 165 kohms and significantly lower than the polyacrylamide based electrode of Comparative Example B at 785 kohms, demonstrating that the zwitterionic materials maintain both low bench AAMI "electricals" and skin impedance under low humidity conditions.

Without being limited to the foregoing, the claims follow.

What is claimed is:

1. A hydrophilic pressure sensitive adhesive composition comprising: a zwitterionic polymer and sufficient plasticizer to render pressure sensitive adhesive, the composition.

2. The adhesive composition of claim 1, wherein the zwitterionic polymer is prepared from at least one zwitterionic monomer.

3. The adhesive composition of claim 1, wherein the zwitterionic polymer is selected from the group consisting of a homopolymer and a copolymer of at least one zwitterionic monomer and a hydrophilic comonomer.

4. The adhesive composition of claim 2, wherein the zwitterionic monomer is selected from the group consisting of 3-dimethyl (methacryloyloxyethyl) ammonium propanesulfonate; 3-dimethyl (acryloyloxyethyl) ammonium propanesulfonate; 1,1-dimethyl-1-(3-methacrylamidopropyl)-1-(3-sulfopropyl)-ammonium betaine; and combinations thereof.

5. The adhesive composition of claim 3, wherein the zwitterionic monomer is selected from the group consisting of 3-dimethyl (methacryloyloxyethyl) ammonium propanesulfonate; 3-dimethyl (acryloyloxyethyl) ammonium propanesulfonate; 1,1-dimethyl-1-(3-methacrylamidopropyl)-1-(3-sulfopropyl)-ammonium betaine; and combinations thereof.

6. The adhesive composition of claim 3, wherein the hydrophilic comonomer is selected from the group consisting of acrylamide; acrylic acid; methacrylic acid; 2-hydroxyl ethylacrylate; 2-hydroxyl propylacrylate; N,N-dimethylaminoethyl acrylate; N-vinyl pyrrolidone; N,N-dimethyl acrylamide (NNDMA), and combinations thereof.

7. The adhesive composition of claim 5, wherein the hydrophilic comonomer is selected from the group consisting of acrylamide; acrylic acid; methacrylic acid; 2-hydroxyl ethylacrylate; 2-hydroxyl propylacrylate; N,N-dimethylaminoethyl acrylate; N-vinyl pyrrolidone; N,N-dimethyl acrylamide (NNDMA); and combinations thereof.

8. The adhesive composition of claim 7, wherein the zwitterionic monomer comprises from about 20 to about 95 weight percent of the zwitterionic polymer.

9. The adhesive composition of claim 1, wherein the zwitterionic monomer is selected from the group consisting of N-(3-carboxypropyl)-N-methacrylamido-(ethyl-N,N-dimethyl) ammonium betaine and 1,1-dimethyl-1-[2-methacryloyloxyethyl]-1-[2-carboxyethyl]-ammonium betaine.

10. The adhesive composition of claim 1, wherein the plasticizer comprises from about 30 to about 90 weight percent of the adhesive composition.

11. The adhesive composition of claim 1, wherein the composition further comprises an electrolyte, an antimicrobial agent, a therapeutic agent, or a penetration enhancing agent, or combinations thereof.

12. The adhesive composition of claim 1 further comprising a compatible polymer to form a blend.

13. The adhesive composition of claim 12, wherein the compatible polymer comprises up to 40 weight percent of the blend, and wherein the adhesive composition comprises from about 1 to to about 10 weight percent of the blend.

14. The adhesive composition of claim 13, wherein the compatible polymer is selected from the group consisting of poly(ethylene-oxide), poly(acrylic acid), poly(N-vinyl pyrrolidone), poly(vinyl alcohol), and poly(acrylamide).

15. A biomedical electrode, comprising:
   a field of adhesive conductive medium for contacting mammalian skin and a means for electrical communication for interfacing with the adhesive conductive medium and electrical diagnostic, therapeutic, or electrosurgical instrumentation, the adhesive conductive medium adhered to the means for electrical communication and comprising an adhesive composition according to claim 1.

16. The biomedical electrode according to claim 15, wherein the adhesive conductive medium further comprises an ionic salt electrolyte present in an amount from about 0.5 to about 5 weight percent of the adhesive conductive medium.

17. The biomedical electrode according to claim 15, wherein the adhesive conductive medium further comprises a redox couple present in an amount of not more than about 20 percent by weight of the adhesive conductive medium.

18. The biomedical electrode according to claim 15, wherein the means for electrical communication comprises a conductor member having an interface portion contacting the adhesive conductive medium and a tab portion available for mechanical and electrical contact with the electrical diagnostic, therapeutic, or electrosurgical instrumentation.

19. The biomedical electrode according to claim 15, wherein the means for electrical communication comprises a conductor member having an eyelet or snap connector contacting the adhesive conductive medium.

20. The biomedical electrode according to claim 15, wherein the means for electrical communication comprises a conductive member having a conductive layer coating at least on a side of the conductor member contacting the adhesive conductive medium.

21. The biomedical electrode according to claim 20, wherein said conductive layer coating is silver/silver chloride.

22. A mammalian skin covering comprising: an adhesive layer for contacting mammalian skin and backing layer, the adhesive layer adhered to the backing layer and comprising a pressure sensitive adhesive composition according to claim 1.

23. The mammalian skin covering according to claim 22, wherein the adhesive layer further comprises an antimicrobial agent.

24. The mammalian skin covering according to claim 22, wherein the backing layer comprises a film, substrate, or elastic, porous or breathable woven or nonwoven material.

25. The mammalian skin covering according to claim 24, wherein the covering comprises a medical tape, a wound dressing, a bandage of general medicinal utility, or a medical device contacting mammalian skin.

26. A pharmaceutical delivery device comprising: an adhesive layer for contacting mammalian skin and a backing layer, the adhesive layer adhered to the backing layer and comprising a pressure sensitive adhesive composition according to claim 1.

27. The pharmaceutical delivery device according to claim 26, wherein the adhesive layer further comprises a topical, transdermal, or iontophoretic therapeutic agent or pharmaceutical.

28. The pharmaceutical delivery device according to claim 26, wherein the adhesive layer further comprises an excipient, a solvent, or a penetration enhancing agent.

* * * * *